United States Patent [19]
Orgill et al.

[11] Patent Number: 6,117,444
[45] Date of Patent: *Sep. 12, 2000

[54] POLYETHYLENE GLYCOL/ MICROFIBRILLAR COLLAGEN COMPOSITE SERVES AS A RESORBABLE HEMOSTATIC AGENT

[75] Inventors: Dennis P. Orgill, Belmont; John Mulliken, Brookline; Frederick W. Ehret, Malden, all of Mass.

[73] Assignee: Brigham & Women's Hospital, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/835,649

[22] Filed: Apr. 10, 1997

[51] Int. Cl.⁷ .............................. A61F 2/28; A61K 47/30
[52] U.S. Cl. ......................... 424/426; 514/772.3
[58] Field of Search .......................... 424/426; 514/772.3

[56] References Cited

U.S. PATENT DOCUMENTS

| | | |
|---|---|---|
| 2,772,999 | 12/1956 | Masci et al. . |
| 2,793,976 | 5/1957 | McKinney . |
| 3,742,955 | 7/1973 | Battista et al. . |
| 4,186,448 | 2/1980 | Brekke . |
| 4,291,013 | 9/1981 | Wahlig et al. . |
| 4,439,420 | 3/1984 | Mattei et al. . |
| 4,440,789 | 4/1984 | Mattei et al. . |
| 4,443,430 | 4/1984 | Mattei et al. . |
| 4,515,637 | 5/1985 | Cioca . |
| 4,806,621 | 2/1989 | Kohn et al. . |
| 4,863,974 | 9/1989 | Mallouk et al. . |
| 4,913,903 | 4/1990 | Sudmann et al. . |
| 4,983,585 | 1/1991 | Pennell et al. . |
| 5,156,839 | 10/1992 | Pennell et al. . |
| 5,324,519 | 6/1994 | Dunn et al. . |
| 5,464,471 | 11/1995 | Whalen et al. . |
| 5,595,735 | 1/1997 | Saferstein et al. ................ 424/94.64 |
| 5,595,751 | 1/1997 | Bezwada et al. ................ 424/426 |

FOREIGN PATENT DOCUMENTS

| | | |
|---|---|---|
| 183136 | 11/1984 | European Pat. Off. . |
| 383363 | 8/1990 | European Pat. Off. . |
| 560014 | 9/1993 | European Pat. Off. . |
| 2410477 | 6/1979 | France . |
| WO 9639203 | 12/1996 | WIPO . |

OTHER PUBLICATIONS

Baldauf, R., et al. (1986) "The Use of Bone Wax", *J. Foot Surg.*, 25(6):456–458.

Blanche, C., et al. (1988) "The Use of Absorbable Microfibrillation Collagen to Control Sternal Bone Marrow Bleeding", *Int. Surg.*, 73:42–43.

Finn, M. et al. (1992) "Osseous Regeneration in the Presence of Four Common Hemostatic Agents", *J. Oral Maxillofac Surg.*, 50:608–612.

(List continued on next page.)

*Primary Examiner*—Carlos A. Azpuru
*Attorney, Agent, or Firm*—Lahive & Cockfield, LLP; Giulio A. DeConti, Esq.

[57] ABSTRACT

A resorbable hemostatic agent comprising a delivery component, that aids in the delivery to the wound site, and a microfibrillar hemostatic component that controls bleeding in solid tissue and does not delay or interfere with healing is described. The viscosity of this resorbable hemostatic agent can be changed to allow for easy application at a range of temperatures. The resorbable hemostatic agent of the invention provides a biodegradable, biocompatable hemostatic agent which effectively controls bleeding in bone and other dense tissue without interfering with the subsequent healing of the tissue.

26 Claims, 6 Drawing Sheets

OTHER PUBLICATIONS

Friedman, R. et al. (1996) "Saline Made Viscous with Polyethylene Glycol: A New Alternate Breast Implant Filler Material", *Plastic & Reconctructive Surg.* 98(7):1208–1213.

Geary, J. et al. (1950) "New Absorbable Hemostatic Bone Wax," *Annals of Surg.*, 132:1128–1137.

Harris, P. et al. (1980) "Clinical Experiance in Neurosurgery with Absele," *Surg. Neurol.* 13:231–235.

Harris, W. et al. (1978) "Topical Hemostatic Agents for Bone Bleeding in Humans," *J. Bone & Joint Surg.*, 60A(4):454–456.

Köndell, P., et al. (1988) "Absele® in Bone Hemostasis—a clinical and experimental Investigation," *Swed. Dent. J.*, 12:85–90.

Sohleim, E. et al. (1991) "Effect of Local Hemostatics on Platelet Aggregation," *Eur. Surg. Res.*, 23:45–50.

Zirna, H. et al. (1987) "Topical Hemostatic Agents to Reduce Bleeding from Cancellous Bone Surfaces: A Comparision of Gelfoam Paste and Bone Wax," *J. Foot Surg.*, 26(6):496–500.

POLYETHYLENE GLYCOL/ MICROFIBRILLAR COLLAGEN COMPOSITE SERVES AS A RESORBABLE HEMOSTATIC AGENT

BACKGROUND

It is beneficial to control bleeding during surgery in order to maintain adequate vision during the procedure and to avoid the serious complications incurred by blood loss. Although there are many ways to control bleeding in soft tissue, methods to acheive hemostasis in bony tissues have been limited. Furthermore, existing methods employing conventional bone wax can interfere with subsequent healing of the bony tissues.

One of the earliest solutions of hemostasis in bone was developed by Horsley and Squire. Horsley published the composition of his "antiseptic wax" as: seven parts beeswax, one part almond oil, and 1% salicylic, sterilized by boiling (Horsley, V. (1892), *Brit Med J.*, 1: 1165). First report of this agent's clinical use to control bleeding from bone was made by Parker (Parker, R. (1892), *Brit Med J*, 1: 1076–7). Despite the great surgical advances of the century, current bone wax is remarkably similar to Horsley's composition: 88% refined beeswax and 12% isopropylpalmitate. (Baldauf, R. and I. Kanat (1986), *J Foot Surg.*, 25: 456–458). Conventional bone wax has no inherent hemostatic quality; its effect is via tamponade of marrow spaces. The material is not resorbed by the adjacent bone or local surrounding tissues. Therefore, it can induce inflammatory response and inhibit bone regeneration. Furthermore, bone wax may lower the bacterial clearance in cancellous bone (Johnson, P. and Fromm, D. (1981), *Surgery*, 89(2): 206–9), or result in wax embolization (Robicsek, F. et al. (1981), *Ann Thorac Surg.*, 31(4): 357–9).

Although there have been some advances in the area of hemostatic agents for skeletal tissue, conventional bone wax continues to be the most commonly used hemostatic agent. Thus, the need exists for a composition that can easily be delivered to an osteotomy gap and that controls hemostasis of bone without delaying or inhibiting bone repair. There exists a need for an effective resorbable bone agent that has inherent hemostatic qualities, is easily delivered to the site, is compatible with osseous repair and is biodegradable.

SUMMARY OF THE INVENTION

This invention provides a resorbable hemostatic agent that is easily applied to the site of solid tissue bleeding and, further, controls hemostasis without limiting or delaying the subsequent healing of the tissue. The invention features a delivery component that can exist in either a semi-solid form or liquid form at temperatures ranging from 0° C. to 45° C. The change in viscosity of the delivery component at varying temperatures allows for straightforward, uncomplicated application of the hemostatic agent to the wound. Once the composition is delivered to the wound in solid or semi-solid form, the increased temperature of the body causes the delivery component to become less viscous. This aids faster reabsorbtion into the adjacent bone and surrounding tissues. In a preferred embodiment, the delivery component is water soluble delivery agent, such as polyethylene glycol.

In one aspect of the invention, the delivery component comprises about 65% to about 95% by weight of the resorbable hemostatic agent, preferably about 70% to about 95% by weight.

In another aspect of the present invention, the delivery component comprises a combination of a high molecular weight and a low molecular weight polyethylene glycol. Preferably, the resorbable hemostatic bone agent contains about 84% high molecular weight polyethylene glycol and about 9% to about 10% low molecular weight polyethylene glycol. However, the proportions of high molecular weight and low molecular weight polyethylene glycols can be adjusted in order to provide easy application even when the temperature of the body being treated is elevated or reduced.

The resorbable hemostatic agent of this invention can further be used for treatment of defects to dense tissues other than bone. The hemostatic agent can also be used, for example, as a plug in bleeding muscle tissue.

The invention also features a resorbable hemostatic component in microfibrillar or microcrystilline form for controlling hemostasis at the wound site. This component also adheres to the bone tissue pores and does not interfere with subsequent osseous repair. A preferred hemostatic component is microfibrillar collagen (MFC). This component has been found not to retard bone healing, and after delivery, it is slowly degraded and resorbed by surrounding tissue. The resorbable hemostatic agent can comprise about 5% to about 25% by weight MFC, preferably 5% to 20% by weight MFC, and most preferably about 6% to about 7% by weight MFC.

The present invention can also contain a biologically active healing adjunct or bone inducing or regenerating agent to further aid in the process of bone repair.

DETAILED DESCRIPTION OF THE INVENTION

Figure 1:
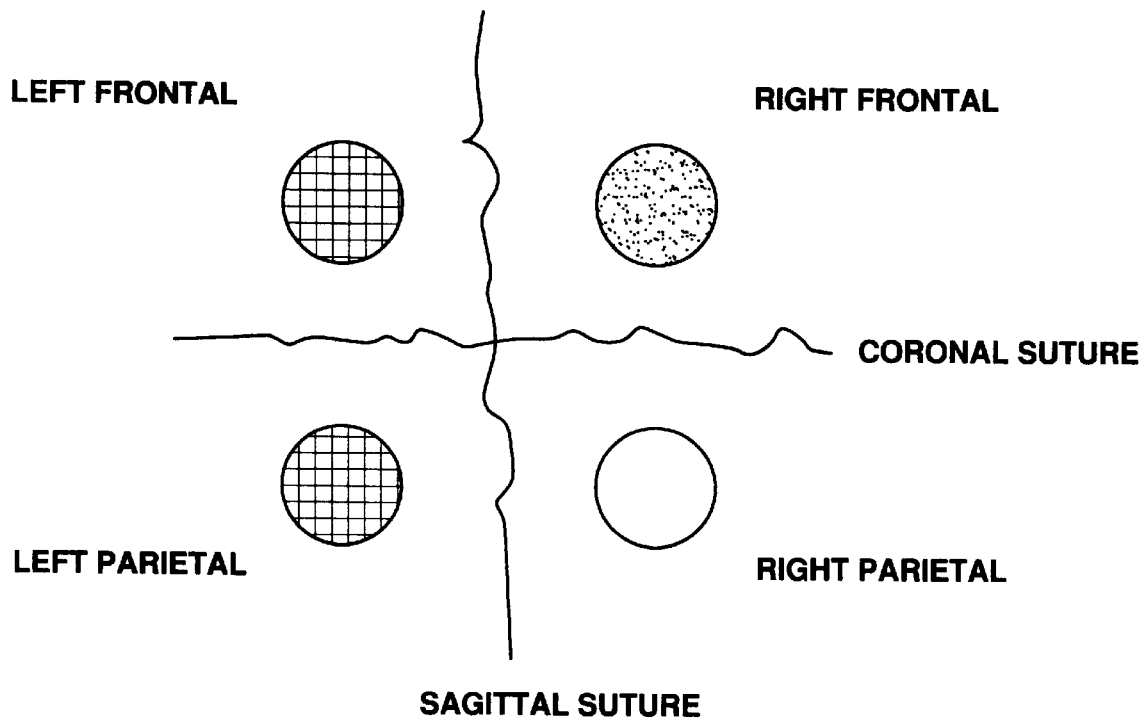
FIG. 1 illustrates the operative site, showing four 5 mm holes in frontal and parietal bones.

This invention features a resorbable hemostatic agent comprising a delivery component, that aids in the case of delivery to the wound site, and a microfibrillar hemostatic component that controls bleeding in solid tissue and that does not delay or interfere with healing. When used for the treatment of bony defects, it does not interfere with subsequent bone repair. The delivery component can exist in semi-solid or liquid form at temperatures ranging from 0° C. to 45° C. As used herein, the term semi-solid" is intended to encompass viscous states ranging from a liquid to a stiff paste. The ability of the delivery component to change viscosity at varying temperatures allows for uncomplicated application of the resorbable bone agent in a malleable, semi-solid form to an osseous defect. Upon application to the wound site, the resorbable agent is subjected to elevated body temperature which causes the delivery component to become less viscous. In less viscous form, the delivery component is quickly reabsorbed into adjacent bone and surrounding body tissue. Thus, the delivery component's limited presence at the wound site, unlike conventional bone wax, does not inhibit bony union.

Polyethylene glycol (PEG) is particularly useful as the delivery component due to its water solubility, biocompatability, and ability to change from solid to liquid form at increased temperatures. As described in the following Example, it has been found that polyethylene glycol is reabsorbed within several hours after the application of the hemostatic agent of the invention to bleeding bone. Since the polyethylene glycol is rapidly removed, the resorbable hemostatic agent allows for fresh blood and macrophages to infiltrate the wound site. The resorbable hemostatic bone agent can comprise about 65% to about 95% by weight of the delivery component, preferably, about 70% to about 95% by weight.

In a preferred embodiment, high molecular weight and low molecular weight polyethylene glycols are combined to form the delivery component. By combining low molecular weight polyethylene glycol, which is in liquid form at room temperature, with high molecular weight polyethylene glycol, which is a solid at room temperature, the delivery component takes on a malleable consistency. Preferably, the resorbable hemostatic composition comprises about 84% by weight high molecular weight polyethylene glycol and about 9% to about 10% by weight low molecular weight polyethylene glycol. However, the consistency of the resorbable hemostatic bone agent can be adjusted by varying the percentages of high molecular weight and low molecular weight polyethylene glycol. The percentages of high molecular weight polyethylene glycol in the resorbable hemostatic agent can range from about 70% to about 90% by weight. The low molecular weight polyethylene glycol can comprise about 10% to about 30% by weight of the resorbable agent.

The resorbable hemostatic agent of this invention can further be used as a plug for the treatment of wounds in other dense tissues, such as muscle. For example, bleeding from puncture wounds in skeletal muscle can be stopped by filling the wound with the resorbable hemostatic agent. In addition, the viscosity of the resorbable hemostatic agent can be adjusted for treatments in which the body is exposed to elevated or reduced temperatures. For example, during cardiopulmonary bypass surgery, the body temperature is lowered to reduce the heart rate. By increasing the proportion of low molecular weight polyethylene glycol and reducing the proportion of high molecular weight polyethylene glycol, a less viscous hemostatic "plug" can be easily applied to the cold tissue. After the procedure, as the body temperature returns to normal, the polyethylene glycol is rapidly reabsorbed by the surrounding tissue.

Various low molecular weight polyethylene glycols and various high molecular weight polyethylene glycols can be used to vary the consistency of the resorbable bone wax. Low molecular weight polyethylene glycols can include, for example, polyethylene glycol with an average molecular weight ranging from about 300 to about 600. The high molecular weight polyethylene glycols can include polyethylene glycol with an average molecular weight ranging from about 1000 to about 1500. Preferably, PEG 400 and PEG 1450 are used in combination.

The microfiberous quality of the hemostatic component has been found to permit easy combination with the delivery component. It is also beneficial since the microfiberous nature of the hemostatic component allows for it to catch in the pores of the bleeding bone and in between the fiber bundles of wounded muscle tissue. In addition the microfiberous quality of the hemostatic agent provides a higher surface to volume ratio with the wounded tissue. In a preferred embodiment, microfibrillar collagen (MFC) is the hemostatic component. MFC has been discovered to be effective at stopping bleeding from bone while eliciting minimal inflammatory response. In addition, MFC is easily embedded into cancellous bone when polyethylene glycol is the delivery agent. Once in place, MFC does not interfere with osteogenesis. Furthermore, MFC has been shown to be slowly removed from the wound site by natural healing processes over approximately a two month period.

In another aspect of the invention, the resorbable hemostatic bone agent can also comprise a biologically active healing adjunct or bone inducing or regenerating substance to further aid in the process of bone repair. The term "healing adjunct", as used herein, refers to biologically active substances, such as antibiotics and anti inflammatory drugs, that can aid in preventing infection or inflammatory response. Antibiotics can include, for example, streptomycin, tetracycline, penicillin and ampicillin. Anti-inflammatory drugs can include, for example, indomethacin. The term "bone inducing substance" or "bone regenerating substance", as used herein, refers to substances that can be used to aid in the process of bone repair. For example, calcium phosphate can be used as a bone inducing substance.

This invention is further illustrated by the following Example which should not be construed as limiting.

EXAMPLE

We blended PEG with microfibrillar collagen (84% polyethylene glycol 1450 and 9.3% polyethylene glycol 400 and 6.7% microfibrillar collagen by weight) and compared it to commercial bone wax in full-thickness cranial defects in New Zealand white rabbits.

Preparation of Polyethylene Glycol/MFC Hemostatic Agent

Preparation of the composite was done by sterilizing the PEG in an autoclave, while still in a liquid state it was added to MFC (Collastat®) using sterile technique under a laboratory hood.

Polyethylene glycol was supplied by Sigma Chemical Company; the specifications for molecular weights used in our composite are listed below:

| Specifications (Sigma Chemical Company) | | | | |
|---|---|---|---|---|
| Polyethylene Glycols, Carbowax ® | Average Molecular Weight | Freezing Point ° C. | pH at 25° C., 5% Aqueous Solution | Viscosity at 210° F., Centistokes |
| 400 | 380 to 420 | | 4.5 to 7.5 | |
| 1450 | 1300 to 1600 | 43.0 to 46.0 | 4.5 to 7.5 | 25 to 32 |

Preparation of Drill Hole Models

Twenty-one white New Zealand rabbits (2.8–5.0 Kg) were kept in a facility, accredited by the American Association for the Accreditation of Laboratory Animal Care, and provided food pellets and water ad libitum. An intramuscular injection of 3.0–5.0 cc of Atropine (0.08 mg/ml) Xylazine (6 mg/ml), and Ketamine (50 mg/ml was administered. The scalp hair was removed with electric clippers and the skin was prepped with 70% ethanol. A midline incision extending from parietal to nasal region was made and the scalp and periosteum was retracted laterally to expose the calvaria. A #6 round bur on a cordless low-speed drill (Dremel) run at 10,000 RPM was used to create four 5 mm diameter holes in the left and right frontal and parietal bones (FIG. 1). During drilling, the site was irrigated with 0.9% NaCl solution to reduce thermal damage. The defects were obtained by angling the bit to cut through the inner cortical plate at the circumference of the hole and removing the remaining button of cortical plate with a discoid/cleoid instrument. The quality of the defect and condition of the animal was noted as "good hole", "dura tear", or "bone bleed". Care was taken to avoid trauma to the dura.

Treatment of Bone Defects with Polyethylene Glycol/MFC composition

The four defects were copiously irrigated prior to treatment. The defects were filled with equal volumes of one of two treatments, or left empty as a control. The two treatments included commercial bone wax (Ethicon®) and the PEG/MFC composite prepared as previously described. The volume of treatment used was that which could be compressed into a #4 amalgam carrier. This volume, when properly shaped, completely filled the bony defect.

The defects were evaluated at intervals ranging from 8 hours to 85 days. After the allotted healing time had expired, animals were again anesthetized and then euthanized with thiopental via intracardiac injection. The cranial bones were exposed and photographed. A separating disc was used to harvest a block of skull including all four defects, which was subsequently split into four individual samples each containing one defect.

Bone specimens were fixed for at least 3 days in 2% paraformaldehyde, 0.1 M cacodylic buffer, pH 7.4 on a rotating table at 4° C. Specimens were decalcified in 7.5% EDTA in 0.1 M cacodylic buffer, pH 7.4, at 4° C. Samples were placed on a shaker and the solution was changed daily for approximately 3 weeks. Samples were infiltrated with vacuum with catalyzed JB-4 Solution A according to manufacturer's directions (Polysciences, Inc.). Infiltrating solution was changed every day for three days, and then samples remained in the fourth solution for approximately 3 weeks. Samples were embedded in glycol methacrylate (JB-4, Polysciences, Inc.) at a ratio of 1.0 ml Solution B (N,N-dimethylaniline) to 30 ml Solution A (acrylic monomer, n-butoxyethanol). Serial sections, 4 µm thick, were cut transversally in the midportion of the treated defect and stained for 8 minutes with Toluidine Blue 0, pH 4.0.

An observer, masked to the type of treatment, analyzed the samples and used computer planimetry to determine the extent of new bone growth. Bone growth was estimated as percent fill, measuring the area of new bone compared to the original size of the defect. Values are expressed as mean +standard deviation.

Results

Gross Appearance:

This formulation of PEG/MFC agent was initially harder than conventional bone wax but with brief kneading became softer and more malleable than bone wax. The strands of microfibrillar collagen were easily embedded into the lattice of trabeculae of cancellous bone. Both PEG/MFC and conventional bone wax effectively stopped bony bleeding caused by drilling. All animals survived to sacrifice, with no evidence of infection or hematoma.

Analysis of the defects showed that the polyethylene glycol composite was completely resorbed at time of the earliest biopsy, taken at 8 hours (n=2). Defects sampled on or before two weeks (n=12) contained a visible amount of MFC. The residual MFC was surrounded by fresh blood, mesenchymal tissue, and macrophages. Little or no MFC was observed in wounds sampled between two weeks and 55 days (n=26) and no MFC was present in specimens examined after day 55 (n=4).

Figure 2:
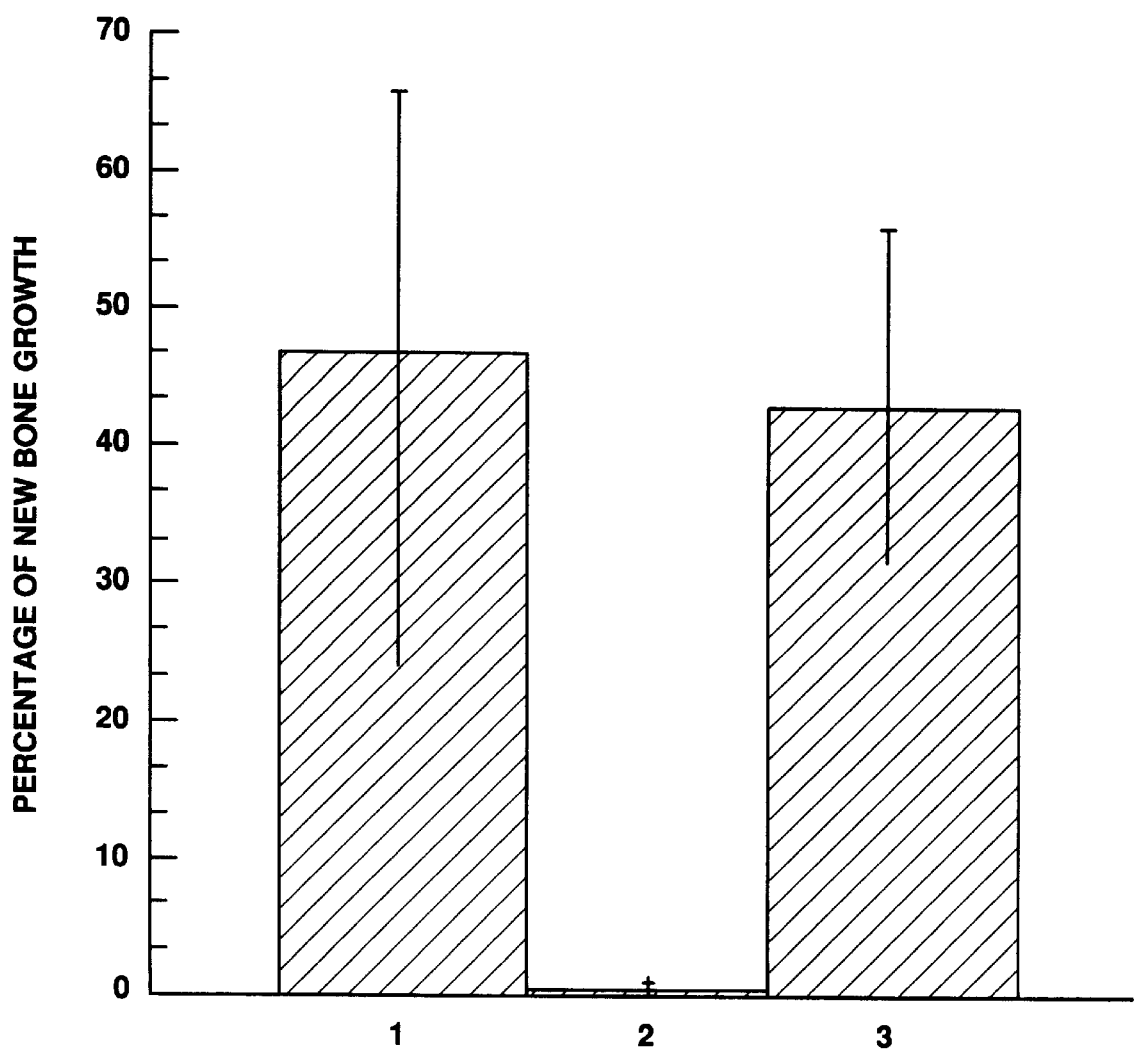
FIG. 2 demonstrates the average percentage of bone growth, measured as percent fill of original defects, in conventional bone wax and PEG/MFC agent treated defects versus open control defects, at Day 29.

The conventional bone wax was grossly present in all defects in which it was placed (n=10). However, wax was not directly observed in histological sections due to melting that occurred during slide processing. Defects treated with bone wax evidenced very little bony regeneration (FIG. 2). Biopsies taken on Day 29 showed no new bone growth (n=6). Infiltration was limited to a moderate number of macrophages in granulation tissue lining the border of the defect. Granulation tissue was evident throughout the 85-day study.

Figure 3:
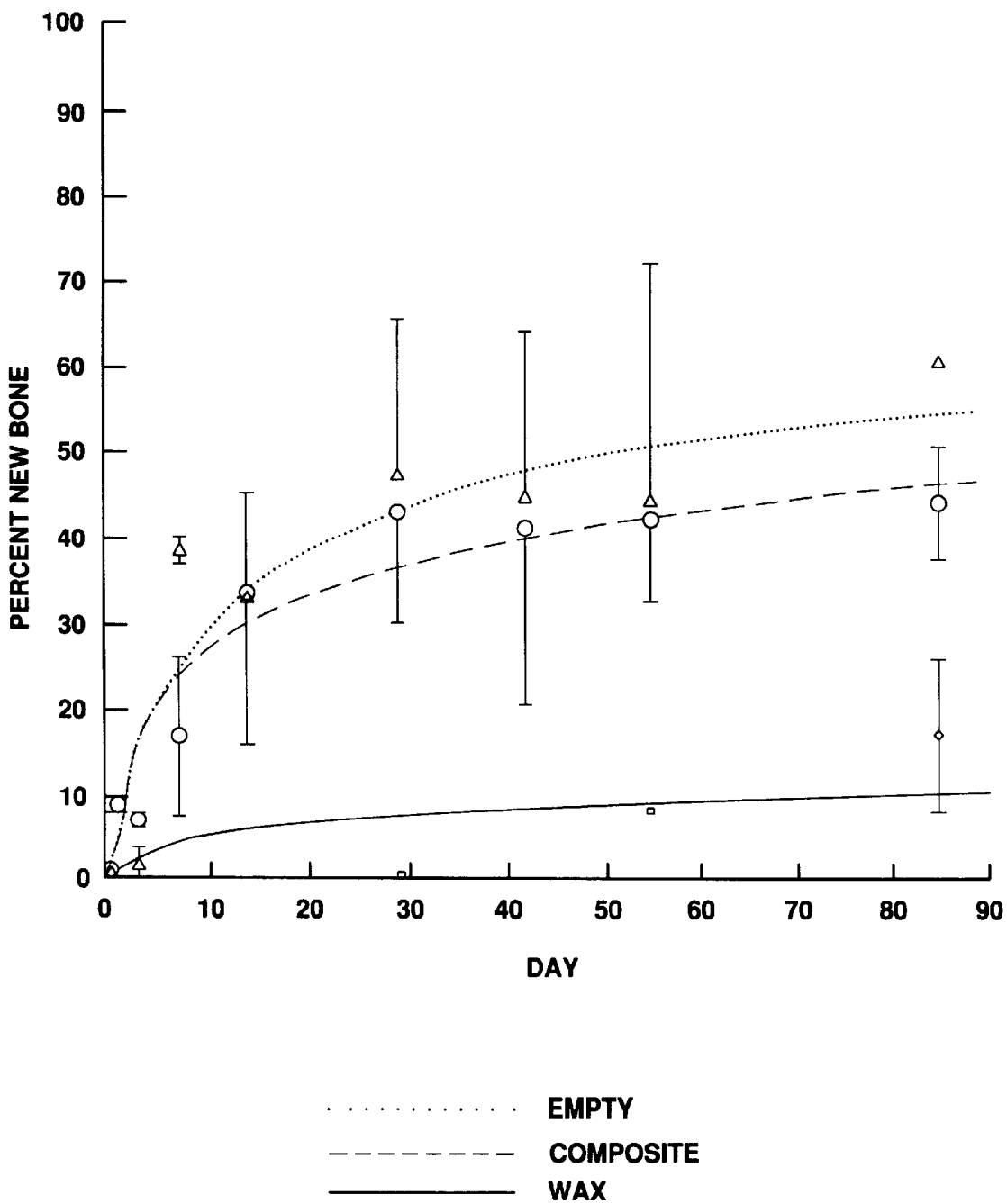
FIG. 3 illustrates bone growth over the 85 day study for conventional bone wax and PEG/MFC agent treated defects and unfilled defects.
Figure 4A:
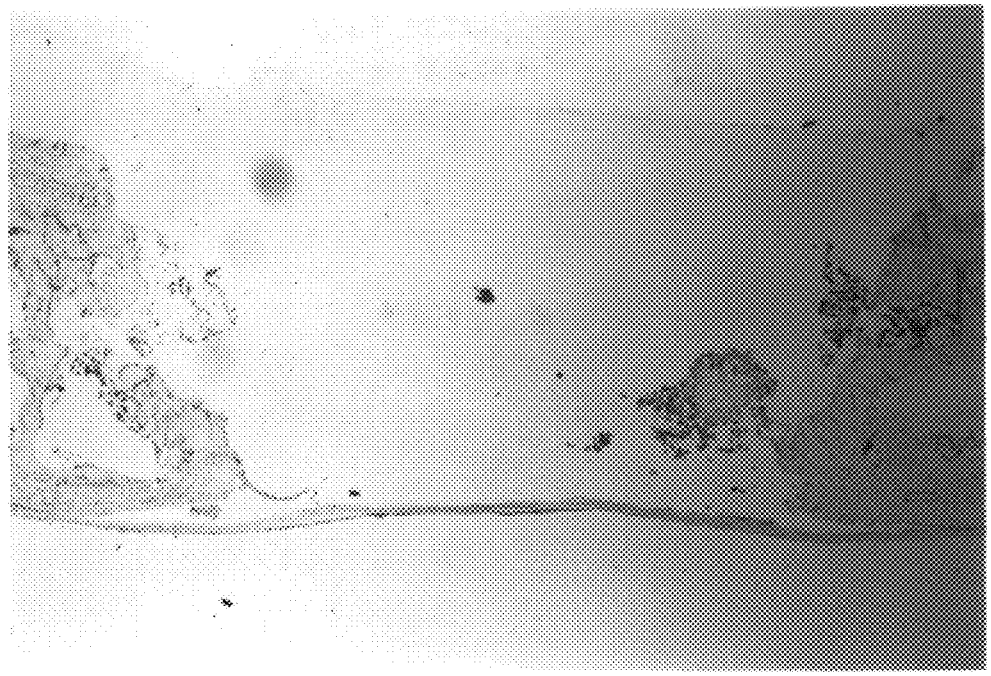
FIG. 4 provides a histologic view of bony defects filled with PEG/MFC agent at Days 0.33, 7, 14, 29, 55, and 85 (4a–4e, respectively). Residual MFC remains in lower left corner of defect at 8 hr. (4a). By day 7, bone growth from margins of defect is evident and residual MFC remains in upper right corner of defect (4b). At day 14, fibrous union achieved as spongy bone growth increases, some MFC present at the base of the defect (4c). At day 29, bony islands have formed and MFC has been resorbed (4d). At day 55, fat cells fill upper portion of defect, bone remodeling evident and no MFC observed (4e).
Figure 4B:
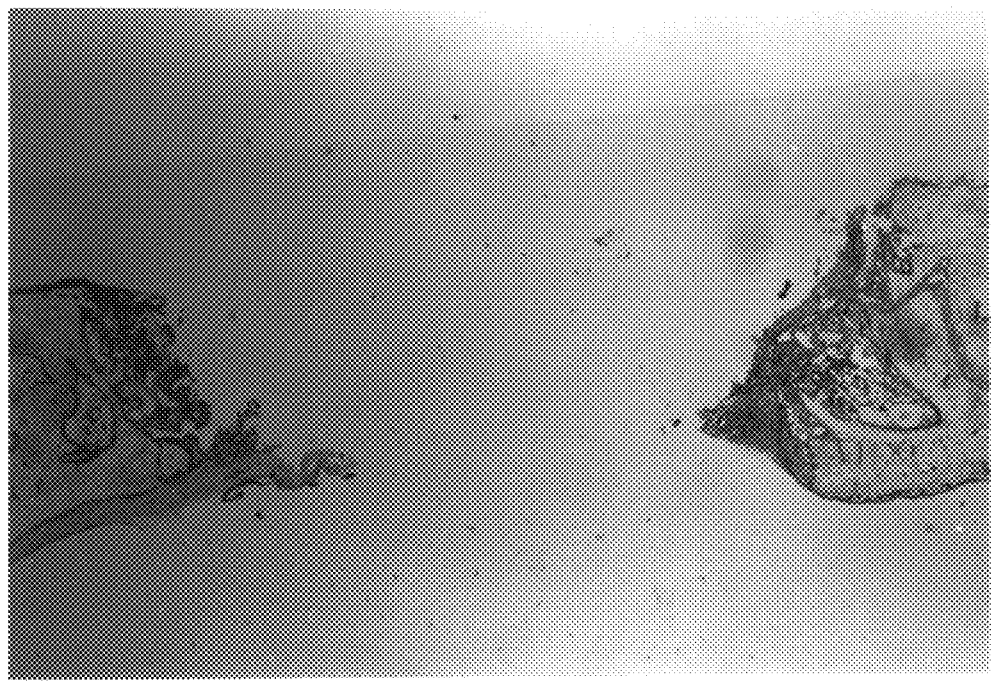
Figure 4C:
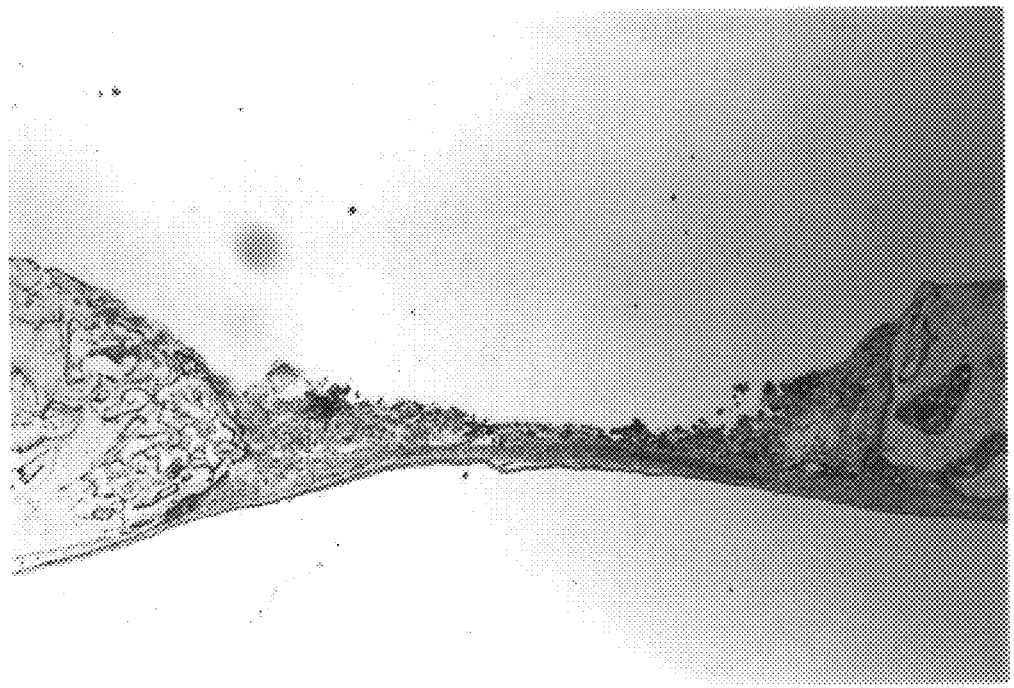
Figure 4D:
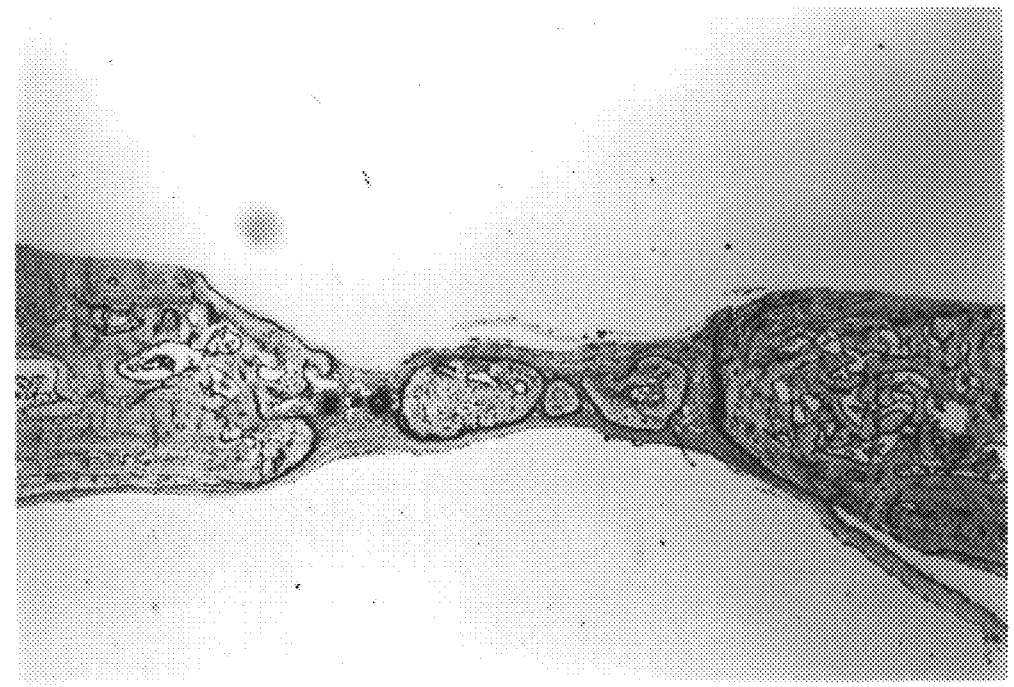
Figure 4E:
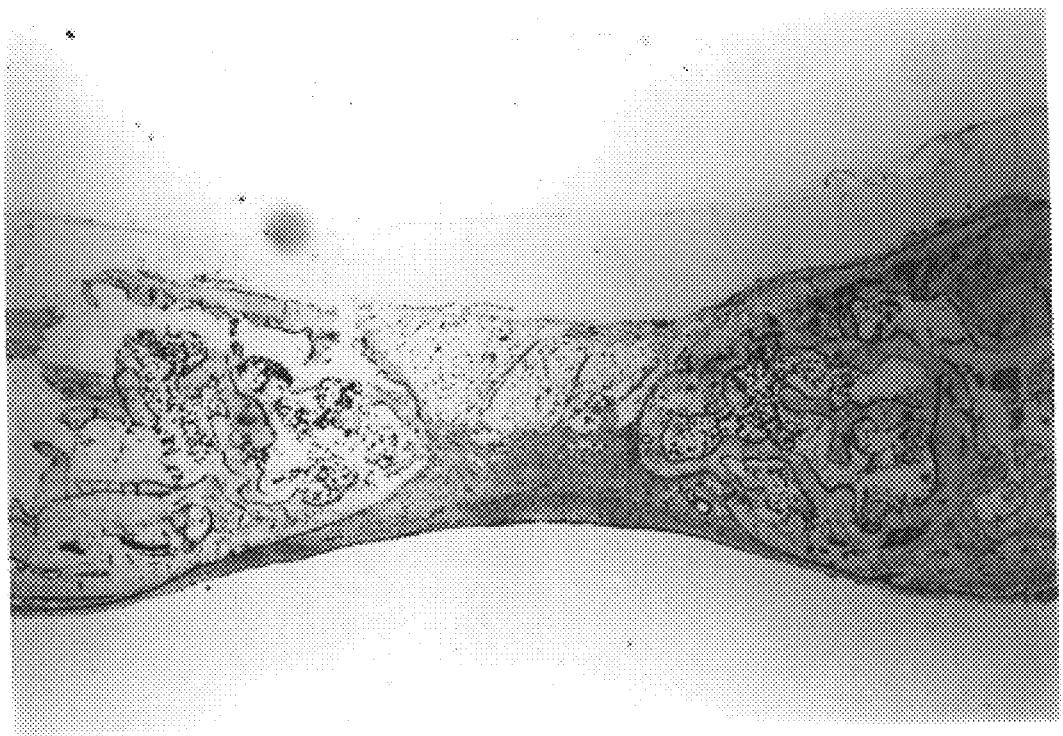

Both PEG/MFC (n=2) and unfilled specimens (n=2) demonstrated rapid osteoblastic activity with periosteal proliferation beginning by Day 3 and the formation of woven bone and bony islands by Day 7 (n=2,2, respectively). Fibrous tissue crossed most defects by two weeks. In PEG and untreated wounds, the percent of new bone increased to day 29, after which time there was no significant difference in the amount of bony growth between the PEG/MFC treated defects, 43±13% (n=18), and the untreated defects, 47±19% (n=12) (FIG. 3). Between days 29–85, new bone filled from 41±21%–44±7% of the defect area for PEG/MFC defects (n=30) and 44±28%–60±0% for untreated defects (n=20). During this time frame, 2 of 30 PEG/MFC treated defects achieved complete bony union and 5 of 20 control defects reached bony union (FIG. 4). None of the ten bone wax treated defects evidenced bony union.

There were no gross or histologic signs of infection in any of the wounds during the study period. No giant cells were observed in PEG/MFC or control defects and very few were observed in bone wax treated sites.

These data demonstrate the compatibility of the PEG/MFC composite with bony ingrowth and repair. Bony union can also be inhibited by foreign material such as conventional bone wax. PEG is water soluble and was shown to be resorbed within 8 hours, whereas microfibrillar collagen (MFC) was slowly removed over a two-month period. None of the defects filled with conventional bone wax showed any evidence of healing.

We claim:

1. A resorbable hemostatic bone agent comprising about 65% to about 95% by weight delivery component and about 5% to about 25% by weight hemostatic component, wherein said hemostatic component consists essentially of a microfibrillar collagen and wherein said delivery component is in a semi-solid state at temperatures ranging from 0° C. to 45° C.

2. A resorbable hemostatic bone agent of claim 1 wherein said delivery component comprises a high molecular weight polyethylene glycol and a low molecular weight polyethylene glycol.

3. A resorbable hemostatic bone agent of claim 2 wherein said high molecular weight polyethylene glycol comprises a polyethylene glycol with an average molecular weight ranging from about 1000 to about 1450.

4. A resorbable hemostatic bone agent of claim 2 wherein said low molecular weight polyethylene glycol comprises a polyethylene glycol with an average molecular weight ranging from about 300 to about 600.

5. A resorbable hemostatic bone agent of claim 1, further comprising an antibiotic or anti-inflammatory drug.

6. A resorbable hemostatic bone agent of claim 5 wherein said antibiotic is selected from a group consisting of streptomycin, tetracycline, penicillin and ampicillin.

7. A resorbable hemostatic bone agent of claim 1, further comprising a bone-inducing substance.

8. A resorbable hemostatic bone agent comprising about 70% to about 95% by weight delivery component and about 5% to about 20% by weight hemostatic component, wherein said hemostatic component consists of microfibrillar collagen and wherein said delivery component comprises, in combination, a higher molecular weight and a low molecular weight polyethylene glycol.

9. A resorbable hemostatic bone agent of claim 8 wherein said high molecular weight polyethylene glycol comprises a polyethylene glycol with an average molecular weight ranging from about 1000 to about 1450.

10. A resorbable hemostatic bone agent of claim 8 wherein said low molecular weight polyethylene glycol comprises a polyethylene glycol with an average molecular weight ranging from about 300 to about 600.

11. A resorbable hemostatic bone agent of claim 8, further comprising an antibiotic or anti-inflammatory drug.

12. A resorbable hemostatic bone agent of claim 11 wherein said antibiotic is selected from a group consisting of streptomycin tetracycline, penicillin and ampicillin.

13. A resorbable hemostatic bone agent of claim 8, further comprising a bone-inducing substance.

14. A resorbable hemostatic bone agent comprising about 84% by weight high molecular weight polyethylene glycol, about 9% to about 10% by weight low molecular weight polyethylene glycol and about 6% to about 7% by weight microfibrillar collagen.

15. A resorbable hemostatic bone agent of claim 14 wherein said high molecular weight polyethylene glycol comprises a polyethylene glycol with an average molecular weight ranging from about 1000 to about 1450.

16. A resorbable hemostatic bone agent of claim 14 wherein said low molecular weight polyethylene glycol comprises a polyethylene glycol with an average molecular weight ranging from about 300 to about 600.

17. A resorbable hemostatic bone agent of claim 14, further comprising an antibiotic or anti-inflammatory drug.

18. A resorbable hemostatic bone agent of claim 17 wherein said antibiotic is selected from a group consisting of streptomycin, tetracycline, penicillin and ampicillin.

19. A resorbable hemostatic bone agent of claim 14, further comprising a bone-inducing substance.

20. A biodegradable osteogenic composition for treatment of bone defects, said composition comprising polyethylene glycol and microfibrillar collagen.

21. A resorbable hemostatic agent for treatment of defects in dense tissues, wherein said resorbable hemostatic agent comprises about 65% to about 95% by weight delivery component and about 5% to about 25% by weight hemostatic component, wherein said hemostatic component consists of microfibrillar collagen and wherein said delivery component comprises high molecular weight and low molecular weight polyethylene glycol.

22. A resorbable hemostatic agent of claim 21 wherein said dense tissues include muscle and bone.

23. A resorbable hemostatic agent of claim 21 wherein said high molecular weight polyethylene glycol comprises a polyethylene glycol with an average molecular weight ranging from about 1000 to about 1450.

24. A resorbable hemostatic agent of claim 21 wherein said low molecular weight polyethylene glycol comprises a polyethylene glycol with an average molecular weight ranging from about 300 to about 600.

25. A resorbable hemostatic agent of claim 21, further comprising an antibiotic or anti-inflammatory drug.

26. A resorbable hemostatic agent of claim 21 wherein said antibiotic is selected from a group consisting of streptomycin, tetracycline, penicillin and ampicillin.

\* \* \* \* \*